US008535931B2

(12) United States Patent
Yadan et al.

(10) Patent No.: US 8,535,931 B2
(45) Date of Patent: Sep. 17, 2013

(54) NON-PHOTOSYNTHETIC MICRO-ORGANISMS ENRICHED WITH ORGANIC SELENIUM FROM SELENO-HYDROXYACID COMPOUNDS AND APPLICATIONS THEREOF IN THE FIELD OF NUTRITION, COSMETICS AND PHARMACUEUTICALS

(75) Inventors: Jean-Claude Yadan, Montreuil Sous Bois (FR); Marc Moutet, Cachan (FR)

(73) Assignee: Tetrahedron, Vincennes (FR)

( * ) Notice: Subject to any disclaimer, the term of this patent is extended or adjusted under 35 U.S.C. 154(b) by 219 days.

(21) Appl. No.: 13/060,970

(22) PCT Filed: Aug. 28, 2009

(86) PCT No.: PCT/EP2009/061165
§ 371 (c)(1),
(2), (4) Date: Feb. 25, 2011

(87) PCT Pub. No.: WO2010/023291
PCT Pub. Date: Mar. 4, 2010

(65) Prior Publication Data
US 2011/0151545 A1 Jun. 23, 2011

(30) Foreign Application Priority Data
Aug. 29, 2008 (FR) ..................................... 08 55825

(51) Int. Cl.
*C12N 1/20* (2006.01)
*C12N 1/16* (2006.01)
*C12N 1/00* (2006.01)

(52) U.S. Cl.
USPC ..................... 435/252.9; 435/243; 435/252.1; 435/252.21; 435/252.7

(58) Field of Classification Search
USPC ............ 435/243, 252.1, 252.21, 252.7, 252.9
See application file for complete search history.

(56) References Cited

U.S. PATENT DOCUMENTS

| 5,639,482 A | 6/1997 | Crary |
| 6,197,295 B1 | 3/2001 | Hsia et al. |
| 2005/0089530 A1 | 4/2005 | Moesgaard et al. |
| 2007/0258964 A1 | 11/2007 | Andreoni et al. |

FOREIGN PATENT DOCUMENTS

| CN | 1283171 | | 2/2001 |
| CN | 1302723 | | 7/2001 |
| CN | 1778199 | A | 5/2006 |
| CN | 1810161 | A | 8/2006 |
| CN | 1817143 | A | 8/2006 |
| DE | 198558670 | A1 | 6/2000 |
| EP | 1 602 716 | A1 | 12/2005 |
| GB | 2 216 421 | A | 10/1989 |
| JP | 7300409 | A | 11/1995 |
| KR | 950006950 | B1 | 6/1995 |
| KR | 20040101145 | A | 12/2004 |
| RU | 2209237 | C2 | 7/2003 |
| TW | 565432 | B | 12/2003 |
| WO | WO 03/078605 | A1 | 9/2003 |
| WO | WO 2006/008190 | A2 | 1/2006 |
| WO | WO 2006008190 | A2 * | 1/2006 |

OTHER PUBLICATIONS

Schulz et al. 200. Bacterial volatiles: the smell of small organisms. Journal of the Royal Society of Chemistry, vol. 24, pp. 814-842.*
Calomme et al. 1995. *Selenium* and *Lactobacillus* species. Journal of Applied Bacteriology, vol. 79, pp. 331-340).*
International Search Report issued in application No. PCT/EP2009/061165 on Oct. 9, 2009.
Alzate et al., "Comparison of Biotransformatino of Inorganic Selenium by *Lactobacillus* and *Saccharomyces* in Lactic Fermentation Process of Yogurt and Kefir," J. Agric. Food Chem ., 2008, pp. 8728-8736, vol. 56, No. 18.
Andreoni et al., "Selenite tolerance and accumulation in the *Lactobacillus* species," Annals of Microbiology, 2000, pp. 77-88, vol. 50.
Avoscan et al., "Selno-L-Methionine Is the Predominant Organic Form of Selenium in *Cupriavidus metallidurans* CH34 Exposed to Selenite or Selenate," Appl. Environ. Microbiol., Sep. 2006, pp. 6414-6416, vol. 72, No. 9.
Calomme et al., "Seleno-Lactobacillus, An Organic Selenium Source," Biol. Trace Element Res., 1995, pp. 379-383, vol. 47.
Dumont et al., "Selenium speciation from food source to metabolites: a critical review," Anal. Bioanal. Chem., 2006, pp. 1304-1323, vol. 385.
Infante et al., "Selenium speciation analysis of selenium-enriched supplements by HPLC with ultrasonic nebulisation ICP-MS and electrospray MS/MS detection," J. Anal. At Spectrom., 2004, pp. 1529-1538, vol. 19.
McSheehy et al., "Determination of Methionine and Selenomethionine in Selenium-Enriched Yeast by Species-Specific Isotope Dilution with Liquid Chromatography—Mass Spectrometry and Inductively Coupled Plasma Mass Spectrometry Detection," Anal. Chem., Jan. 2005, pp. 344-349, vol. 77, No. 1.
Mester et al., "Certification of a new selenized yeast reference material (SELM-1) for methionine, selenomethinone and total selenium content and its use in an intercomparison exercise for quantifying these analytes," Anal. Bioanal. Chem., 2006, pp. 168-180, vol. 385.
Möller H., "The Chemistry of Natural and Synthetic Skin Barrier Lipids," Cosmetic Lipids and the Skin Barrier, Thomas Forster, Ed., 2002, pp. 1-3.
Mony et al., "RenalBioavailability of Selenium After Supplementation With Different Forms of Selenium: Ion Probe and Mass Spectrometry Study," J. Trace Elements in Experimental Med., 2000, pp. 367-380, vol. 13.

(Continued)

*Primary Examiner* — Jon P Weber
*Assistant Examiner* — Kailash C Srivastava
(74) *Attorney, Agent, or Firm* — Foley & Lardner LLP (57) ABSTRACT

The invention relates to the enrichment of non-photosynthetic micro-organisms with organic selenium, and more particularly with selenomethionine, from a compound of the seleno-hydroxyacid type such as 2-hydroxy-4-methylseleno-butanoic acid in the (D, L) form or in the form of an enantiomer, salt, ester, or amide derivative of said compound, and to the use of micro-organisms, particularly bacteria thus enriched in the fields of animal or human nutrition, cosmetics, or pharmaceuticals.

8 Claims, 3 Drawing Sheets

(56) References Cited

OTHER PUBLICATIONS

Müller et al., "The path of unspecific incorporation of selenium in *Escherichia coli*," Arch. Microbiol., 1997, pp. 421-427, vol. 168.

Schrauzer G.N., "Nutritional Selenium Supplements: Product Types, Quality, and Safety," Commentary, J. Amer. College of Nutrition, 2001, pp. 1-4, vol. 20, No. 1.

Von Stockhausen H.B., "Selenium in Total Parenteral Nutrition," Biolog. Trace Element Res., 1988, pp. 147-155, vol. 15.

Wendel A., "Biochemical Functions of Selenium," Phosphorus, Sulfur, and Silicon, 1992, pp. 405-415, vol. 67.

Xia et al., "Enriched Selenium and Its Effects on Growth and Biochemical Composition in *Lactobacillus bulgaricus*," J. Agric. Food Chem., 2007, pp. 2413-2417, vol. 55, No. 6.

\* cited by examiner

NON-PHOTOSYNTHETIC MICRO-ORGANISMS ENRICHED WITH ORGANIC SELENIUM FROM SELENO-HYDROXYACID COMPOUNDS AND APPLICATIONS THEREOF IN THE FIELD OF NUTRITION, COSMETICS AND PHARMACUEUTICALS

The invention relates to the enrichment of non-photosynthetic micro-organisms with organic selenium, especially thanks to compounds of the seleno-hydroxyacid type, and more particularly with 2-hydroxy-4-methylseleno-butanoic acid, in the (D, L) form, or in the form of an enantiomer, salt, ester or amide derivative of said compound, and to the use of micro-organisms thus enriched in the fields of animal or human nutrition, cosmetics or pharmaceuticals.

Selenium is an essential micro-nutrient for humans and especially mammals (Wendel, A.; *Phosphorus, Sulfur Silicon Relat Elem.;* 1992; 67, 1-4, 405-415). In particular, it participates, in the form of L(+)-selenocysteine or L(+)-selenomethionine (Mutter, S. et al.; *Arch. Microbiol,* 1997; 168; 421) in the biosynthesis of selenoproteins such as Glutathione peroxydase, Thioredoxin reductase and Selenoprotein P.

In humans, selenium deficiencies have been reported, especially in the case of patients subject to feeding by parenteral route over long periods (Von Stockhausen, H. B.; *Biol. Trace Elem. Res.;* 1988; 15; 147-155). A daily supplement of 200 µg of selenium is considered as safe and adequate for an adult male of average weight (Schrauzer, G. N., *J. Am. Col. Nutr.;* 2001; 20; 1-14).

Selenium is found in nature in two forms: organic and inorganic.

Inorganic compounds are most usually salts such as sodium selenite or selenate. These compounds are very toxic for humans and most animals.

Organic compounds (organo-selenium compounds) are represented in living organisms especially by the amino acids L(+)-selenomethionine, L(+)-methylselenocysteine and L(+)-selenocysteine.

L(+)-selenomethionine is the principal source of organic selenium in humans and in animals. However, humans and animals are autoxotrophic for this amino acid, which can only be obtained through diet.

It is thus in this organic form that selenium should ideally be incorporated in food supplements aiming to treat or prevent selenium deficiency.

It has thus been demonstrated that a supplementation of the diet with L(+)-selenomethionine is much less toxic and has a better bioavailability than an intake in the form of sodium selenite (Mony, M C et al.; *J. of Trace Elem. Exp. Med.;* 2000; 13; 367-380).

At present, other metabolic routes for capturing selenium by living organisms are not known apart from those using as substrates inorganic selenium, principally in the form of sodium selenite, and selenomethionine.

A suitable supply of organic selenium can be found in the higher plants (wheat, maize, soya especially), in which more than 80% of the selenium is constituted by L(+)-selenomethionine (Schrauzer, G. N.; *J. Am. Coll. Nutrit;* 2001; 20; 1; 1-4). However the selenium concentration in these plants is not sufficient to be able to produce easily, and at less cost, food additives.

One of the paths explored to obtain compositions rich in selenium consists in enriching certain micro-organisms with organic selenium from inorganic selenium. These micro-organisms, once enriched, can serve as raw materials for the preparation of food products or cosmetics.

Numerous publications describe the preparation of yeasts enriched with selenium, and more particularly the yeast *Saccharomyces cerevisiae* (Oh Tae-Kwang et al., patent KR950006950 of 26 Jun. 1995) so as to use them as such or incorporate them in food compositions (Moesgaard S. et al., patent DK200200408 of 16 Sep. 2003); or instead to obtain derivative products enriched with selenium such as bread (Wang Boaquan, patent CN 1817143 of 16 Aug. 2006), milk (Jeng Chang-Yi, patent TW565432 of 11 Dec. 2003), eggs (Cui Li et al., patent CN1302723C of 7 Mar. 2007), chocolate (In Gyeong Suk et al., patent KR20040101145 of 8 Nov. 2004) or beer (Jakovleva L. G. et al., patent RU2209237 of 27 Jul. 2003) enriched with selenium. In the field of health foods, preparations containing yeasts enriched with selenium have also been proposed for pregnant women (Wang Weiyi, patent CN 1778199 of 31 May 2006), or instead to improve the intestinal micro-environment of hypoglycemic patients (Li Tao Zhao, patent CN1810161 of 2 Aug. 2006). In the dermocosmetics field, compositions containing yeasts enriched with selenium have been developed so as to reduce hair loss (Kasik Heinz, patent DE19858670 of 21 Jun. 2000) or in preventing photo-ageing (Kawai Norihisa et al., patent JP07300409 of 14 Nov. 1995). Pharmaceutical preparations containing yeasts enriched with selenium have been used in the prevention and the treatment of inflammatory pathologies such as the retinopathies linked to diabetes (Crary Ely J., patent U.S. Pat. No. 5,639,482 of 17 Jun. 1997), or cardiovascular pathologies (Nagy P. L. et al.; patent HUT060436 of 28 Sep. 1992).

Bacteria and more particularly probiotic bacteria have, also, been subject to enrichment with selenium (Calomme M. et al., *Biol. Trace Elem. Res.;* 1995; 47; 379-383). *Lactobacillus acidophilus*, but also *Lactobacillus reuteri, Lactobacillus ferintoshensis, Lactobacillus buchneri/parabuchneri* (Andreoni V. et al., U.S. Pat. No. 258,964) have been described as food supplements enriched with selenium. A study of *Lactobacillus casei* ssp *casei* has however shown that selenium is incorporated mainly in the form of selenocysteine (Calomme M. et al., *Biological Trace Element Research* 1995, 47, 379-383). Mixtures of probiotics constituted of yeasts and lactobacilla, so as to reinforce the immune system and disease resistance (Huang Kehe Qin, patent CN1283171C of the 8 Nov. 2006), have been prepared.

However, in all of these preparations, the micro-organisms enriched with selenium are prepared from inorganic selenium uniquely. Thus, the source of selenium the most often used consists in sodium selenite or selenate solubilised in culture media of micro-organisms. The micro-organisms thereby enriched, although having synthesised satisfactory quantities of organic selenium assimilable by the human body, often have a high residual level of non-transformed inorganic selenium, which can prove to be dangerous for the consumer. In addition, the bacteria, such as those of the genus *Lactobacillus*, mainly transform this inorganic selenium into selenocysteine and not into selenomethionine.

In a preceding application published under WO 2006/008190, the applicant has described novel organic compounds of seleno-hydroxyacid type that can serve as precursors for the synthesis of L(+)-selenomethionine in humans and animals.

In a surprising manner, the applicant has observed that organic compounds of seleno-hydroxyacid type described in the application WO 2006/008190, incorporated in the culture media, could be used by different micro-organisms such as bacteria and yeasts for the purpose of their enrichment with organic selenium. The results obtained have revealed that these compounds make it possible to enrich very efficiently non-photosynthetic micro-organisms with organic selenium, and more particularly with selenomethionine with an equivalent, or even superior, yield to that obtained with inorganic compounds normally used such as sodium selenite.

It has thus appeared that the enrichment of micro-organisms with selenomethionine from organic compounds of seleno-hydroxyacid type makes it possible to produce micro-organisms containing mainly the source of selenium the most bio-available for humans and animals and practically exempt of inorganic selenium. The invention thus makes it possible to resolve the problems of toxicity linked to the methods of the prior art by reducing the inorganic selenium content and having available new micro-organisms enriched with selenomethionine.

The non-photosynthetic micro-organisms thus enriched may be used directly in the diet in the context of the prevention or the treatment of selenium deficiencies, especially for the purpose of producing pharmaceutical, nutritional or cosmetic products and compositions.

FIGURES

FIGS. 1 to 6 hereafter represent graphs showing the evolution of the growth of micro-organisms over time, in YPG (*Saccharomyces cerevisiae*) or MRS (*Lactobacillus casei*) medium supplemented with different inorganic (sodium selenite) and organic (selenomethionine or 2-hydroxy-4-methylseleno-butanoic acid) (THD-177) selenium compounds. The X-axis corresponds to the number of hours of culture, the Y-axis to the cellular density (absorbance measured at 550 nm).

DETAILED DESCRIPTION OF THE INVENTION

The present application is limited to obtaining non-photosynthetic micro-organisms, in other words micro-organisms whose growth does not depend directly on a light source.

The experimental results obtained within the scope of the present invention concern more particularly non-photosynthetic bacteria and yeasts, which have a very different metabolism to photosynthetic micro-organisms.

By micro-organism is understood any living unicellular organism belonging to one of the following Kingdoms: monera, protista, fungi or protozoa, having a eukaryote or prokaryote cellular structure, of microscopic or ultramicroscopic size, having a metabolic and reproduction potential. Said unicellular organisms can be involved in the formation of filaments or biofilms.

By organic selenium is understood a set of organic molecules containing at least one compound having at least one atom of selenium in its chemical structure capable of being produced by a living organism, such as especially the amino acids selenomethionine, methylselenocysteine, selenocystine and selenocysteine, or peptides or proteins containing them.

Preferably, the non-photosynthetic micro-organisms according to the invention are yeasts or bacteria, more preferentially a yeast of the genus *Saccharomyces* or a bacterium of the genus *Lactobacillus*.

The micro-organisms thus enriched with organic selenium may be used as such or instead as a food additive. They may, for example, be dehydrated to form a stable powder that can be incorporated in compositions serving as basis for the preparation of transformed products but can also be used living as probiotics in food product transformation processes.

The object of the present invention is thus a novel method of enrichment of non-photosynthetic micro-organism with organic selenium, characterised in that said non-photosynthetic micro-organism is cultivated in a culture medium comprising a compound of seleno-hydroxyacid type.

Preferably, the compound of seleno-hydroxyacid type is a compound of general formula (I), a salt, or instead an ester or amide derivative thereof,

$$\text{(I)}$$

formula in which:
n=0, 1 or 2;
$R_1$=OH, $OCOR_3$, $OPO_3H_2$, $OPO_3R_4R_5$ or $OR_6$;
$R_2$=OH, $R_3$, $NHR_7$, S-cysteinyl or S-glutathionyl;
it being understood that when n=1 and $R_2$=OH, then $R_1$ cannot be OH;
$R_3$=alkoxyl, ceramide 1, ceramide 2, ceramide 3, ceramide 4, ceramide 5, ceramide 6a and 6b, S-cysteinyl, S-glutathionyl, or a group chosen from the following groups:

OR$_4$=alkoxyl (C$_1$-C$_{26}$), ceramide 1, ceramide 2, ceramide 3, ceramide 4, ceramide 5, ceramide 6a and 6b, or a group chosen from the following groups:

OR$_5$=alkoxyl (C$_1$-C$_{26}$), ceramide 1, ceramide 2, ceramide 3, ceramide 4, ceramide 5, ceramide 6a and 6b, or a group chosen from the following groups:

$OR_6$=pyruvate, lactate, citrate, fumarate, maleate, myristate, palmitate, stearate, palmitoleate, oleate, linoleate, a residue of natural fatty acid or 13-cis retinoate;

$NHR_7$=$NH_2$, NH-alkyl ($C_1$-$C_{26}$), a residue of natural amino acid or a residue of natural amine.

Figure 2:
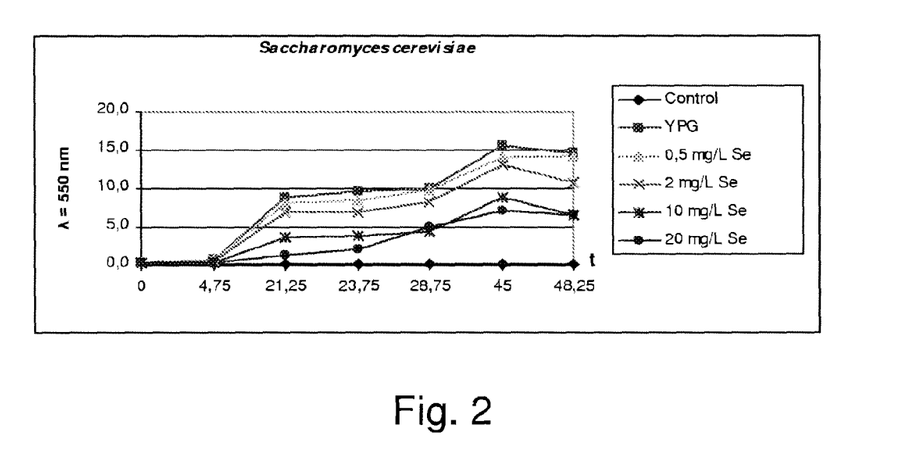
FIG. 2: the yeast *Saccharomyces cerevisiae* is cultivated in YPG medium, supplemented with selenomethionine (organic compound)

In formula (I) above:

by alkyl is understood a group comprising 1 to 26, advantageously 1 to 10, more advantageously 1 to 6, linear or cyclic carbon atoms, optionally branched, optionally fluorinated or polyfluorinated, and comprising optionally one or more carbon-carbon double bonds, such as for example methyl, ethyl, isopropyl, trifluoromethyl, the fatty chains of fatty acids (in other words without the acid function) such as the fatty chain of linoleyl, the fatty chain of linolenyl, the fatty chain of palmitoyl.

by alkoxyl is understood a group derived from a primary, secondary or tertiary alcohol, and bound to the rest of the molecule through the oxygen atom of the alcohol function, comprising 1 to 26, advantageously 1 to 10, more advantageously 1 to 6, linear or cyclic carbon atoms, optionally branched, optionally fluorinated or polyfluorinated, and comprising optionally one or more carbon-carbon double bonds, such as for example methoxyl, ethoxyl, isopropoxyl, trifluoromethoxyl.

radical structures of ceramide type are described especially in "Cosmetic Lipids and the Skin Barrier", Thomas Forster Ed. 2002, Marcel Dekker, Inc., page 2, FIG. 2.

by natural is understood any corresponding compound found in the metabolism of organisms of the plant or animal world, as well as in that of humans (Steglich W., Römpp Encyclopedia Natural Products, G. Thieme ed.)

by fatty acid is understood an aliphatic carboxylic acid comprising from 4 to 28 carbon atoms (including the carbon atom of the carboxylic acid function), the hydrocarbon chain being linear, saturated or unsaturated.

by fatty acid residue, it is understood that the fatty acid is bound to the rest of the molecule through its carboxylic acid function (COOH).

by fatty alcohol, it is understood a fatty acid as defined above in which the carboxylic acid function (COOH) has been replaced by an alcohol function (OH).

by natural amino acid is understood especially the following amino acids: Alanine (Ala), Arginine (Arg), Asparagine (Asn), Aspartic acid (Asp), Cysteine (Cys), Glutamine (Gin), Glutamic acid (Glu), Glycine (Gly), Histidine (His), Isoleucine (He), Leucine (Leu), Lysine (Lys), Methionine (Met), Phenylalanine (Phe), Proline (Pro), Serine (Ser), Threonine (Thr), Tryptophan (Trp), Tyrosine (Tyr) and Valine (Val).

by natural amine, it is understood a natural primary amine bearing an $NH_2$ function such as putrescine, cadaverine, spermine, spermidine.

by residue of amino acid or amine, it is understood that the amino acid or the amine is bound to the rest of the molecule through its primary amine function ($NH_2$).

by oligomer, it is understood any compound constituted of the chaining of 2 to 15 monomers bound together through an ester type bond.

by polymer, it is understood any compound constituted by the chaining of more than 15 monomers bound together through an ester type bond.

According to the invention, said compounds of formula (I) are preferentially used in the form of calcium, magnesium or zinc salts, which enables a better solubility in the culture media, as well as a better assimilation by the micro-organisms.

The invention also encompasses the stereoisomers of compounds of formula (I) as well as the mixtures of stereoisomers in all proportions and in particular in racemic mixtures.

By "stereoisomers" is understood, according to the present invention, diastereoisomers and enantiomers. They are thus optical isomers. Stereoisomers that are not mirror images of each other are designated "diastereoisomers", and stereoisomers that are mirror images of each other, but are not superposable, are designated "enantiomers".

A mixture containing equal quantities of two individual enantiomeric forms of opposite chirality is designated "racemic mixture".

Advantageously, n represents 0 in the general formula (I).

$R_1$ may represent an OH, $OCOR_3$ or $OR_6$ group, with advantageously $R_3$ representing an alkoxyl group. In particular, $R_1$ can represent an OH group.

$R_2$ will represent especially an OH or $R_3$ group, and more particularly an OH or alkoxyl ($C_1$-$C_{26}$) group.

The seleno-hydroxyacid compounds used within the scope of the present invention may correspond more particularly to the following formula:

(1a)

or to a salt, a stereoisomer or a mixture of stereoisomers in all proportions, an ester or an amide thereof, with n as defined previously and preferably representing 0.

By "ester", it is understood that an ester function (—C(O)O—) is formed from an OH group of an alcohol or carboxylic acid function borne by compounds of seleno-hydroxyacid type according to the present invention. These esters are thus obtained:

either by reaction of the alcohol function with a carboxylic acid such as an acid of formula R—COOH with R=alkyl as defined above; a natural fatty acid; a natural amino-acid; glutathione; pyruvic, lactic, citric, fumaric, maleic, or 13-cis-retinoic acid; especially with an acid RCOOH, in particular with R representing a linear or branched, saturated hydrocarbon chain comprising from 1 to 6 carbon atoms, or by reaction of the carboxylic acid function with an alcohol such as a primary, secondary or tertiary alcohol, of formula R'H with R'=alkoxyl as defined above; a fatty alcohol; or a ceramide; especially with an alcohol R'H, in particular with R representing a linear or branched, saturated hydrocarbon chain comprising from 1 to 6 carbon atoms.

By "amide", it is understood that an amide function (—C(O)NH—) is formed from an OH group of an alcohol or carboxylic acid function borne by compounds of seleno-hydroxyacid type according to the present invention. These amides are thus obtained:

either by reaction of the alcohol function with an amide derived from a carboxylic acid as described in the definition of the term "ester", or by reaction of the carboxylic acid function with an amine derived from an alcohol as described in the definition of the term "ester" or corresponding to a natural amino acid or a natural amine.

The invention relates more particularly to the use of a compound of formula (I) chosen from:
L-2-hydroxy-4-methylseleno-butanoic acid,
D-2-hydroxy-4-methylseleno-butanoic acid,
D,L-2-hydroxy-4-methylseleno-butanoic acid,
or a salt of said compounds.

These compounds are described in the application WO 2006/008190.

The object of the invention is also a micro-organism, and more particularly a non-photosynthetic bacterium enriched with organic selenium, capable of being obtained according to the method of the invention. Such a micro-organism generally has an organic selenium content greater than 1000 ppm, preferably greater than 1200 ppm, more preferentially greater than 1400 ppm, in selenium equivalent, and an inorganic selenium content less than 0.5%, preferably less than 0.2% and more preferentially less than 0.1% in dry weight of said micro-organism.

The invention also relates more particularly to a yeast of the genus *Saccharomyces* enriched with selenium, characterized in that it comprises a selenomethionine content greater than 130 microgrammes selenium equivalent per gramme (µgSe/g), preferably greater than 150 µgSe/g and more preferentially greater than 170 µgSe/g in dry weight of said yeast.

The total selenium and selenomethionine content of the micro-organisms may be determined respectively by mineralisation and enzymatic digestion after centrifugation and lyophilisation of the micro-organisms, for example by following the method according to Lobinsky et al. described in Mester, Z. et al. (2006) *Annal. Bioanal. Chem.* 385: 168-180. The selenomethionine content corresponds to the content of selenomethionine as free amino acid and selenomethionine hound to other amino acids, in other words present in proteins and peptides.

A yeast according to the invention may prove to be useful, for example, in the manufacture of bakery products enriched with selenium but also in obtaining milks of animal origin enriched with organic selenium, or instead eggs enriched with organic selenium.

The invention more particularly relates to a non-photosynthetic probiotic bacterium, in particular a lactic bacterium, especially of the genus *Lactobacillus*, characterised in that it comprises a selenomethionine content greater than 50 µgSe/g, preferably greater than 100 µgSe/g and more preferentially greater than 500 µgSe/g in dry weight of said non-photosynthetic probiotic bacterium.

Selenomethionine will represent especially more than 50%, preferentially more than 60% of the total selenium contained in the bacterium.

Such a bacterium may prove to be useful, for example, in the manufacture of fermented milks, such as cheeses or yoghurts, enriched with organic selenium.

By "probiotic" is understood a micro-organism that can be ingested by animals or humans, in living or dead form, and which has a beneficial effect on animals or humans, in nutritional, pharmaceutical or cosmetic terms. In the case of a bacterium, it may be a lactic bacterium, especially of the genus *Lactobacillus*. The bacteria *Cupriavidus metallidurans* and *Ralstonia metallidurans*, used to detoxify soils, do not correspond to this definition.

The non-photosynthetic probiotic bacteria according to the present invention may thus be useful as probiotics, especially in a cosmetic, pharmaceutical or nutritional product.

The non-photosynthetic micro-organisms according to the invention may thus be useful in human nutrition and in animal nutrition, especially so as to obtain secondary derivatives enriched with organic selenium, such as for example milk or eggs.

The invention also relates to the manufacture of probiotic products, for a food, cosmetic or pharmaceutical use, directly from micro-organisms enriched with organic selenium according to the method of the present invention. Said manufacture involves techniques known by those skilled in the art.

According to a particular embodiment of the invention, the micro-organisms initially enriched with organic selenium according to the method of the present invention, living or dead, are incorporated as additives in a given probiotic composition. The micro-organisms do not participate in this case necessarily in the biological transformation of the ingredients present in the composition.

According to another embodiment of the invention, the living micro-organisms are not enriched beforehand with selenium, but enriched as the method of manufacturing the composition from one or more compounds of formula (I) as defined above proceeds, according to the method of the invention. Said compounds of formula (I) are then incorporated in said composition with the other ingredients and non-photosynthetic micro-organisms. The non-photosynthetic micro-organisms may then bring about a bioconversion of the organic selenium compounds actually within the composition to obtain, for example, a dough, the yeasts of which are enriched with organic selenium or instead a fermented milk in which the lactic bacteria are enriched with organic selenium.

In these compositions, a probiotic bacterium as defined previously, is used more particularly, for example a lactic bacterium, especially of the genus *Lactobacillus*.

The organic selenium and derivative products thus obtained are useful in different applications, of which those recalled in the preamble, especially as cosmetic, pharmaceutical or nutritional agents.

The invention also relates to probiotic compositions (for cosmetic, pharmaceutical or nutritional use) comprising one or more micro-organisms enriched with organic selenium according to the invention, and more particularly a probiotic bacterium as defined previously, for example a lactic bacterium, especially of the genus *Lactobacillus*.

By probiotic composition or product is understood a composition or a product comprising a micro-organism, living or dead, used as probiotic as defined above.

The invention further relates to a culture medium for non-photosynthetic micro-organism characterised in that it comprises one or more compounds of formula (I) defined above. Such a culture medium is useful for the implementation of the method of enrichment of micro-organisms with organic selenium according to the invention. In particular, the invention relates to a culture medium comprising at least one compound of formula (I) as defined previously, preferably 2-hydroxy-4-methylseleno-butanoic acid or a salt thereof, or one of its esters or amides or it stereoisomers or mixtures of stereoisomers at a concentration ranging between 0.5 and 2000 mg/L, preferably between 1 and 1000 mg/L, more preferentially between 2 and 500 mg/L, i.e. respectively around between 0.2 and 800 mg/L of said compound in selenium equivalent, preferentially between 0.4 and 400 mg/L of said compound in selenium equivalent, more preferentially between 0.8 and 200 mg/L of said compound in selenium equivalent.

A method of preparing non-photosynthetic micro-organism according to the invention may especially comprise one or more of the following steps:
  preparing a culture medium, preferably a minimal medium, comprising the chemical elements necessary for the growth of said non-photosynthetic micro-organism;
  introducing into the culture medium a compound of formula (I), preferentially 2-hydroxy-4-methylseleno-butanoic acid or a salt thereof as organic source of selenium;
  adjusting the pH of the mixture to a value ranging between 3 and 8;
  placing in culture a pre-culture inoculum of said non-photosynthetic micro-organism in the mixture thereby constituted, at a temperature ranging between 25 and 80° C., under orbital agitation ranging between 100 and 500 rpm, and an atmosphere that may contain from 0 to 20% of oxygen and from 0.5 to 99% of carbon dioxide, preferably for 24 to 96 hours;
  centrifuging the mixture between 4000 and 10 000 rpm for several minutes;
  taking up the cell pellet in physiological water;
  centrifuging again between 4000 and 10 000 rpm for several minutes;
  sterilising the humid cell pellet in which is found the non-photosynthetic micro-organism enriched with selenium;
  The humid cell pellet may be lyophilised or dried in air.

The culture medium may be especially a synthetic or semi-synthetic medium, an enriched medium, or a selective medium.

After centrifugation and lyophilisation of the micro-organisms, the total selenium and selenomethionine contents may be determined, for example, after respectively mineralisation and enzymatic digestion by the method according to Lobinsky, R. et al. described in Mester, Z. et al. (2006) *Anal. Bioanal. Chem.* 385:168-180.

Other characteristics and advantages of the invention are given in the examples given hereafter. The following examples are given solely by way of illustration and cannot in any way limit the scope of the invention.

EXAMPLES

Example 1

Production of the Yeast *Saccharomyces cerevisiae* in a YPG Medium Containing 2-hydroxy-4-methylseleno-butanoic Acid and in a YPG Medium Containing Sodium Selenite Isolation of the Strain *Saccharomyces cerevisiae* 3053 E000

The strain was isolated from a square of a 42 g of bread making yeast of FALA BACKHEFE make, from a batch identified with a DLC 22 Jul. 2007. This yeast was kept in the refrigerator at +4° C. before use, then it was taken up in liquid YPG (Yeast Peptone Glucose) medium. The strain of *Saccharomyces cerevisiae:* 3053-E000 was obtained by spreading on YPG medium in isolated colonies and placed in collection at −80° C. with addition of 10% vol/vol of glycerol as cryoprotective agent.

Composition of the YPG Medium:

| Yeast Extract | 10 g |
| Peptone | 20 g |
| Glucose | 20 g |
| pH | 7.0 |
| Reverse osmosis water, QS | 1 L |

Figure 1:
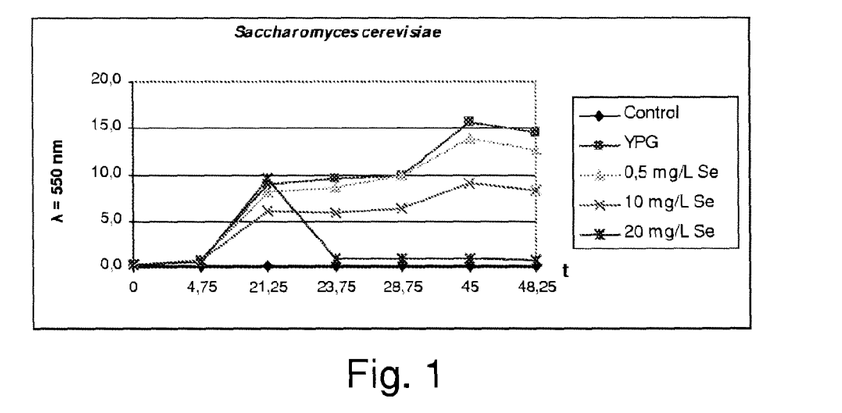
FIG. 1: the yeast *Saccharomyces cerevisiae* is cultivated in YPG medium, supplemented with sodium selenite (inorganic compound)
Figure 3:
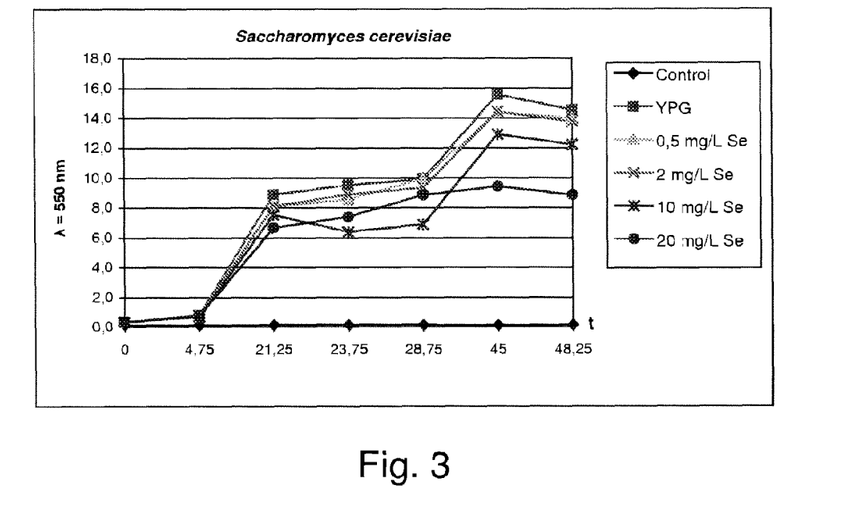
FIG. 3: the yeast *Saccharomyces cerevisiae* is cultivated in YPG medium, supplemented with 2-hydroxy-4-methylseleno-butanoic acid (organic compound according to the invention)

In the experiments described, the growth characteristics of the yeast *Saccharomyces cerevisiae* 3053 E000 were measured in the presence of different concentrations of selenium in the form of sodium selenite, selenomethionine, or 2-hydroxy-4-methylseleno-butanoic acid and compared to the growth characteristics in the absence of additives (control). The pre-culture of the strain *Saccharomyces cerevisiae* 3053-E000 is carried out in liquid YPG medium, at 37° C., under orbital agitation (250 rpm) for 24 h.

Conditions of Culture of the Strain *Saccharomyces cerevisiae* 3053-E000

The culture is formed from an inoculum ($1.10^6$ UFC/ml) of the pre-culture described previously in 100 mL of YPG medium, at pH=4 at a temperature of 37° C. under agitation (250 rpm) and according to the following conditions:

The cultures of *Saccharomyces cerevisiae* 3053-E000 were monitored by absorbance measurements at 550 nm and by CPU counting on YPG gelose plates.

Addition of Selenium in the Form of Sodium Selenite

The concentrations tested for the addition of selenium selenite are 0.5 mg/L, 10 mg/L and 20 mg/L in selenium equivalent, i.e. respectively: 1.1 mg/L, 22.22 mg/L and 44.44 mg/L of sodium selenite.

The graph of FIG. 1 makes it possible to visualise the growth of the strain *Saccharomyces cerevisiae* 3053-E000 in the presence of different concentrations of sodium selenite.

As may be observed, sodium selenite begins to show a toxic effect from 10 mg/L (in selenium equivalent), negatively affecting the rate of growth and the yield of biomass obtained (−50% in 48 h).

At a concentration of 20 mg/L (in selenium equivalent), sodium selenite proves to be very toxic for *Saccharomyces cerevisiae*.

Addition of Selenium in the Form of Selenomethionine

The concentrations tested for the addition of selenomethionine are 0.5 mg/L, 2 mg/L, 10 mg/L and 20 mg/L in selenium equivalent, i.e. respectively 1.25 mg/L, 5 mg/L, 25 mg/L and 50 mg/L of selenomethionine The graph of FIG. 2 makes it possible to visualise the growth of the strain *Saccharomyces cerevisiae* 3053-E000 in the presence of different concentrations of selenomethionine. As may be observed, selenomethionine begins to show an effect from 2 mg/L (in selenium equivalent) negatively affecting the yield of biomass obtained (−29% in 48 h). The increase of the dose to 10 mg/L (in selenium equivalent) produces greater inhibitor effects on the rate of growth and the biomass yield (−50%) without affecting all the same the viability (−30%). For 20 mg/L of selenomethionine (in selenium equivalent), the effects are similar to those obtained for 10 mg/L as regards the rate and the final biomass yield, the toxic effect on the viability being shown more strongly (−50%).

Addition of Selenium in the Form of 2-hydroxy-4-methylseleno-butanoic Acid

The concentrations tested for the addition of 2-hydroxy-4-methylseleno-butanoic acid are 0.5 mg/L, 2 mg/L, 10 mg/L and 20 mg/L in selenium equivalent, i.e. respectively 1.25 mg/L, 5 mg/L, 25 mg/L and 50 mg/L of 2-hydroxy-4-methylseleno-butanoic acid (THD-177, Tetrahedron, France, CAS: 873660-49-2).

The graph of FIG. 3 makes it possible to visualise the growth of the strain *Saccharomyces cerevisiae* 3053-E000 in the presence of different concentrations of 2-hydroxy-4-methylseleno-butanoic acid. As may be observed, the 2-hydroxy-4-methylseleno-butanoic acid begins to show an effect from 10 mg/L (in selenium equivalent) negatively affecting the final biomass yield (−15%) and in reducing the viability by 36%. For a concentration of 20 mg/L of 2-hydroxy-4-methylseleno-acid (in selenium equivalent), the biomass yield is reduced by 36% and the viability is reduced by 50%.

Enrichment with Selenium of *Saccharomyces cerevisiae*

In light of the results obtained previously for the biomass production of the strain *Saccharomyces cerevisiae* 3053-E000, the choice of an incorporation rate of 20 mg/L of 2-hydroxy-4-methylseleno-butanoic acid (in selenium equivalent) and an incorporation rate of 10 mg/L of sodium selenite (in selenium equivalent) in the cultures described hereafter was made:

Pre-cultures: from a culture saturated with YPG, two pre-culture steps were carried out.
Pre-culture 1: 10 mL of culture (inoculation rate 10% v/v from the saturated culture, incubation 24 h at 37° C.)
Pre-culture 2: 100 mL of culture (inoculation rate 10% v/v from the pre-culture 1, incubation 24 h at 37° C.)
Culture: from the pre-culture 2, 1 L of YPG medium is inoculated at a rate of 10% v/v. The culture is incubated at a temperature fixed and regulated at 37° C. The pH is adjusted to 4 and the culture is mixed by orbital agitation (150 rpm).
Preparation of Samples for Analyses:

After 48 hours of culture, the medium is centrifuged at 6500 rpm for 5 minutes, the cell pellet is taken up in physiological water then centrifuged again at 6500 rpm for 5 minutes.

The humid cell pellet is lyophilised for the analysis of selenium constituents (total selenium, selenomethionine and sodium selenite).

Analysis of Selenium Constituents of the Yeast *Saccharomyces cerevisiae* Produced in a Medium Containing 2-hydroxy-4-methylseleno-butanoic Acid or Sodium Selenite The total selenium is assayed by ICP coupled to a mass detection, after mineralisation of the sample. The speciation of the selenium is carried out by high performance liquid chromatography coupled to a mass-mass detection, after enzymatic digestion of the sample (Master, Z. et al. (2006) *Annul. Bioanal. Chem.* 385:168-180).

Results

The concentrations of total selenium, selenomethionine and sodium selenite are given in the following table:

TABLE 1

Analysis of selenium components of the yeast *Saccharomyces cerevisiae* 3053-E000 produced in YPG medium with additives

|  | Total selenium$^a$ | Total selenomethionine$^a$ | Selenomethionine/ Total selenium | Selenite$^a$ |
|---|---|---|---|---|
| Control | 0.17 ± 0.02 | 0.053 ± 0.006 | — | <0.02 |
| +Selenite (10 mgSe/L) | 849 ± 12 | 122 ± 1 | 14% | 14 ± 1 |
| +THD 177 (20 mgSe/L) | 601 ± 15 | 185 ± 21 | 31% | 3.3 ± 0.1 |

$^a$μg (Se equivalent)/g

The results obtained reported in table 1 show that the incorporation of 2-hydroxy-4-methylseleno-butanoic acid in the culture medium makes it possible to enrich by a factor of around 3500 the total selenium content of *Saccharomyces cerevisiae*, selenomethionine constituting 31% of this total selenium. Sodium selenite makes it possible to have a higher enrichment factor, of the order of 5000, but selenomethionine only represents 14% of the total selenium content.

Furthermore, the residual selenite content, in the yeast *Saccharomyces cerevisiae*, linked to the use of 2-hydroxy-4-methylseleno-butanoic acid as selenium source, is more than 4 times less than that corresponding to the use of sodium selenite as selenium source.

2-hydroxy-4-methylseleno-butanoic acid thus indeed constitutes a better selenium source than sodium selenite for enriching with selenomethionine a eukaryote micro-organism such as *Saccharomyces cerevisiae*, while reducing by 400% the risk of toxicity linked to the residual selenite content in the micro-organism.

Example 2

Production of the Bacterium *Lactobacillus paracasei* in a MRS Medium Containing 2-hydroxy-4-methylseleno-butanoic Acid and in a MRS Medium Containing Sodium Selenite Isolation of the strain *Lactobacillus paracasei* 3052 E000

The strain was isolated from a tube of ACTIMEL® sold by the Danone Company.

This tube was kept in the refrigerator at +4° C. before use, then its contents were diluted in 50 mL of liquid MRS medium. The strain of *Lactobacillus paracasei* 3052-E000 was obtained by spreading on MRS medium in isolated colonies. It was characterised on a Galerie API 50 CHL and placed in collection at −80° C. with addition of 10% vol/vol of glycerol as cryoprotective agent.

Composition and Preparation for 1 L of MRS Medium:

| | |
|---|---|
| Polypeptone | 10 g |
| Yeast extract | 5 g |
| Meat extract | 10 g |
| Glucose | 20 g |
| Dibasic potassium phosphate | 2 g |
| Sodium acetate | 5 g |
| Ammonium citrate | 2 g |
| Magnesium sulphate | 0.20 g |
| Manganese sulphate | 0.05 g |
| Tween 80 | 1 ml |
| pH | 6.4 |

Figure 4:
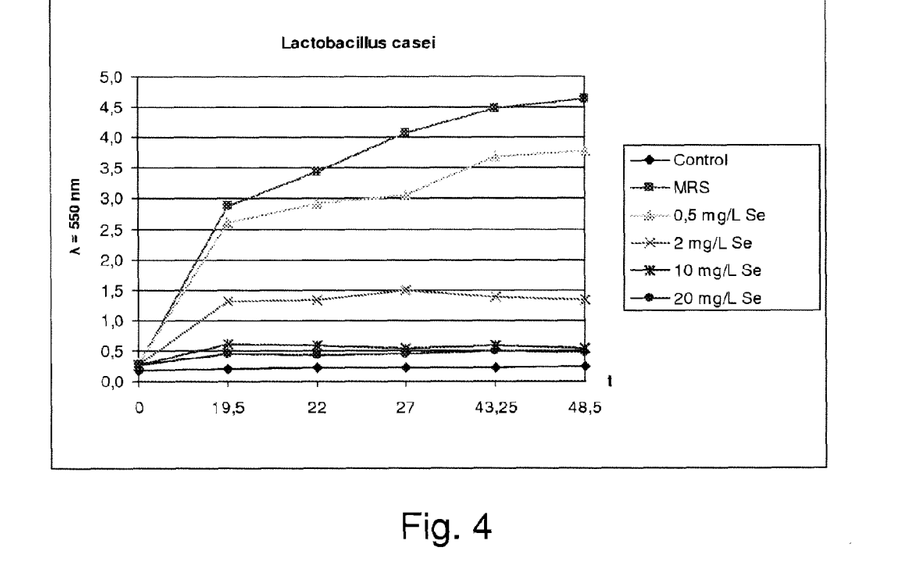
FIG. 4: the bacterium *Lactobacillus casei* is cultivated in MRS medium, supplemented with sodium selenite (inorganic compound)
Figure 5:
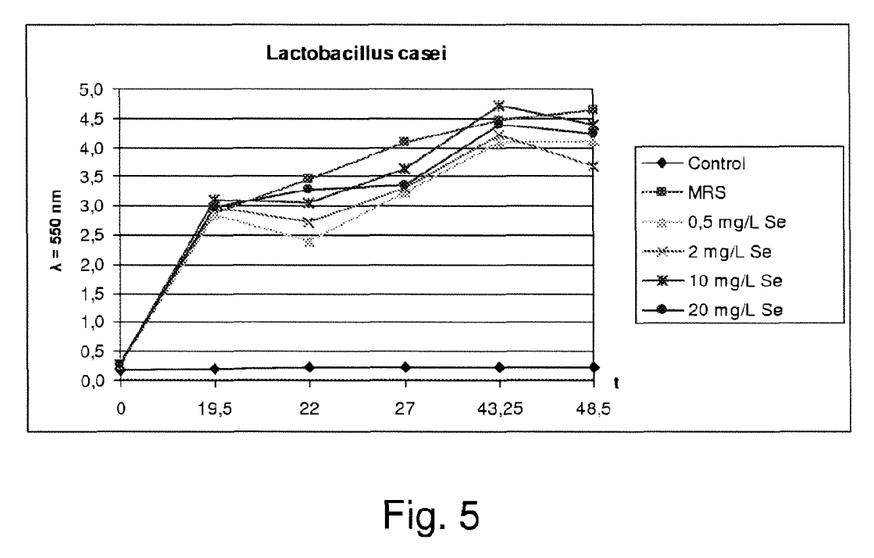
FIG. 5: the bacterium *Lactobacillus casei* is cultivated in MRS medium, supplemented with selenomethionine (organic compound)
Figure 6:
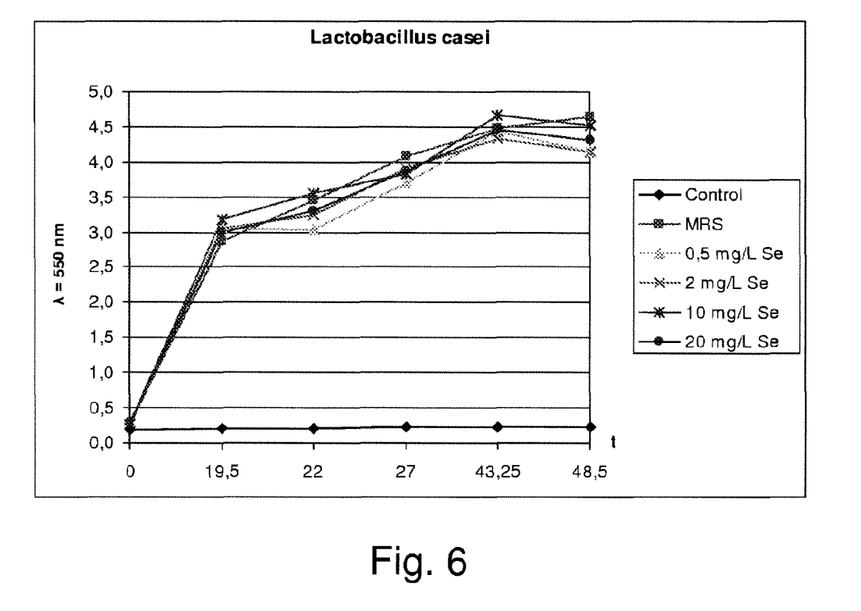
FIG. 6: the bacterium *Lactobacillus casei* is cultivated in MRS medium, supplemented with 2-hydroxy-4-methylseleno-butanoic acid (organic compound according to the invention)

In this experiment, the growth characteristics of the bacterium *Lactobacillus paracasei* were measured in the presence of different concentrations of selenium in the form of sodium selenite, selenomethionine, 2-hydroxy-4-methylseleno-butanoic acid and compared with the growth characteristics in the absence of additives.

Pre-Culture of the Strain *Lactobacillus paracasei* 3052 E000

The pre-culture of the strain *Lactobacillus paracasei* 3052-E000 is carried out in liquid MRS medium, at 42° C., without agitation for 24 h. The culture of the strain *Lactobacillus paracasei* 3052-E000 was carried out from an inoculum ($1.10^7$ UFC/ml) of the above pre-culture in 100 mL of MRS medium, at pH=6.4 and at a temperature of 42° C. (without agitation).

The cultures were monitored by absorbance measurements at 550 nm and CFU counting carried out on MRS plate.

Addition of Selenium in the Form of Sodium Selenite

The concentrations tested for the addition of selenium selenite are 0.5 mg/L, 2 mg/L, 10 mg/L and 20 mg/L in selenium equivalent, i.e. respectively 1.11 mg/L, 4.44 mg/L, 22.22 mg/L and 44.44 mg/L of sodium selenite. The graph of FIG. 4 makes it possible to visualise the growth of the strain *Lactobacillus paracasei* 3052-E000 in the presence of sodium selenite.

As may be observed, sodium selenite begins to show an inhibitor effect on the growth of *Lactobacillus paracasei* from the addition of 0.5 mg/L of sodium selenite (in selenium equivalent), as well as a reduction in the biomass production yield of 25% at 48 h. These effects are accentuated with the addition of 2 mg/L of sodium selenite (in selenium equivalent), to attain a reduction in yield reaching 90% at 48 h for concentrations of 10 and 20 mg/L of selenium selenite (in selenium equivalent). At these levels, sodium selenite shows a toxicity on *Lactobacillus paracasei*.

Addition of Selenium in the Form of Selenomethionine

The concentrations tested for the addition of selenomethionine are 0.5 mg/L, 2 mg/L, 10 mg/L and 20 mg/L in selenium equivalent, i.e. respectively 1.25 mg/L, 5 mg/L, 25 mg/L and 50 mg/L of selenomethionine.

The graph of FIG. 5 makes it possible to visualise the growth of the strain *Lactobacillus paracasei* 3052-E000 in the presence of different concentrations of selenomethionine.

The addition of selenium in the form of selenomethionine does not show an inhibitor effect on the growth, or a noticeable effect of reduction in the biomass production yield up to 20 mg/L (in selenium equivalent) on *Lactobacillus paracasei*, Addition of Selenium in the Form of 2-hydroxy-4-methylseleno-butanoic Acid The concentrations tested for the addition of 2-hydroxy-4-methylseleno-butanoic acid are 0.5 mg/L, 2 mg/L, 10 mg/L and 20 mg/L in selenium equivalent, i.e. respectively 1.25 mg/L, 5 mg/L, 25 mg/L and 50 mg/L of 2-hydroxy-4-methylseleno-butanoic acid (THD-177, Tetrahedron, France, CAS: 873660-49-2).

The graph of FIG. 6 makes it possible to visualise the growth of the strain *Lactobacillus paracasei* 3052-E000 in the presence of different concentrations of 2-hydroxy-4-methylseleno-butanoic acid.

In a manner similar to the addition of selenomethionine, the addition of selenium in the form of 2-hydroxy-4-methylseleno-butanoic acid does not show an inhibitor effect on the growth or noticeable effect of reduction in the biomass production yield up to 20 mg/L of 2-hydroxy-4-methylseleno-butanoic acid (in selenium equivalent).

In order to complete the study of the impact of the addition of 2-hydroxy-4-methylseleno-butanoic acid, at higher values, concentrations of 40 and 60 mg/L were tested under the same conditions as previously.

As for the addition of 20 mg/L of selenium in the form of 2-hydroxy-4-methylseleno-butanoic acid, no inhibitor effect was observed on the growth and the biomass yield of the strain.

Enrichment with Selenium of *Lactobacillus paracasei*

In light of the results obtained previously, the choice of an incorporation rate of 60 mg/L of 2-hydroxy-4-methylseleno-butanoic acid (in selenium equivalent) and an incorporation rate of 1 mg/L of selenium selenite (in selenium equivalent) was made for the production of biomass of the strain *Lactobacillus paracasei* 3 052-E000, Preparation of Samples for Analyses:

After 48 hours of culture, the medium is centrifuged at 6500 rpm for 5 minutes, the cell pellet is taken up in physiological water then centrifuged again at 6500 rpm for 5 minutes.

Analysis of Selenium Constituents of the Bacterium *Lactobacillus paracasei* Produced in a Medium Containing 2-hydroxy-4-methylseleno-butanoic Acid or Sodium Selenite The total selenium is assayed by ICP coupled to a mass detection, after mineralisation of the sample. The speciation of the selenium is carried out by high performance liquid chromatography coupled to a mass-mass detection, after enzymatic digestion of the sample.

Results

The concentrations of total selenium, selenomethionine and sodium selenite are given in the following table:

TABLE 2

Analysis of selenium components of the bacterium *Lactobacillus paracasei* 3052-E000 produced in MRS medium with additives

| | Total selenium[a] | Total Selenomethionine[a] | Selenomethionine/ Total selenium | Selenite[a] |
|---|---|---|---|---|
| Control | 0.18 ± 002 | 0.108 ± 0.006 | — | <0.02 |
| +Selenite (1 mgSe/L) | 120 ± 2 | 17 ± 2 | 14% | <0.5 |
| +THD 177 (60 mg/L) | 1019 ± 19 | 671 ± 117 | 66% | <0.5 |

[a] μg (Se equivalent)/g

The results obtained in table 2 show that the incorporation of 2-hydroxy-4-methylseleno-butanoic acid into the culture medium makes it possible to enrich by a factor of around 5700 the total selenium content of *Lactobacillus paracasei*, selenomethionine constituting 66% of said total selenium. The enrichment factor with total selenium following the incorporation of sodium selenite in the culture medium is very inferior and is only 700, and selenomethionine only representing 14% of the total selenium content.

2-hydroxy-4-methylseleno-butanoic acid thus indeed constitutes a better source of selenium than sodium selenite for enriching with selenomethionine a prokaryote micro-organism such as *Lactobacillus paracasei*.

Example 3

Production of the Bacterium *Lactobacillus plantarum* 3120-E000 in an MRS Medium Containing 2-hydroxy-4-methylseleno-butanoic Acid after 47 h of Culture In this example, the culture conditions are identical to those of example 2. The results corresponding to these works are described in the following table:

TABLE 3

Analysis of selenium components of the bacterium *Lactobacillus plantarum* 3120-EOOO produced in MRS medium with additives

|  | Total selenium[a] | Total selenomethionine[a] | Selenite[a] |
|---|---|---|---|
| Control | 0.289 ± 0.014 | 0.26 ± 0.03 | <0.2 |
| +THD 177 (10 mg/l) | 582 ± 14 | 512 ± 35 | 0.27 ± 0.03 |
| +THD 177 (60 mg/l) | 2015 ± 78 | 1813 ± 152 | 1.4 ± 0.4 | a: µg (Se equivalent)/g

The results obtained in table 3 show that the incorporation of 2-hydroxy-4-methylseleno-butanoic acid into the culture medium, at 10 mg/L or at 60 mg/L, for 47 h makes it possible to enrich with total selenium by a factor of around 2000 or 7000 respectively. These results show moreover that selenomethionine constitutes more than 88% of the total selenium.

Example 4

Production of the Bacterium *Escherichia coli* WT 3121-E000 in a Minimal Medium (M63+Glucose+Methionine) Containing 2-hydroxy-4-methylseleno-butanoic Acid After 48 h of Culture The origin of the strain *Escherichia coli* WT 3121-E000 is the following: *Escherichia coli* K12 (strain 58), CGSC reference number 5587

Composition and Preparation for 1 L of Culture Medium:

| KH$_2$PO$_4$ | 13.6 g |
| KOH | 4.2 g |
| (NH$_4$)$_2$SO$_4$ | 2.0 g |

-continued

| FeSO$_4$, 7H$_2$O | 1.08 mg |
| Thiamine | 1 mg |
| MgSO$_4$, 7H$_2$O | 246 mg |
| Glucose | 4.0 g |
| Methionine | 50.0 mg |
| pH | 7.0 |
| Reverse osmosis water, QS | 1 L |

The results corresponding to these works are described in the following table:

TABLE 4

Analysis of selenium components of the bacterium *Escherichia coli* WT 3121-E000 produced in minimal medium (M63 + glucose + methionine) with additives

|  | Total selenium[a] | Total selenomethionine[a] | Selenite[a] |
|---|---|---|---|
| Control | 0.164 ± 0.140 | 0.140 ± 0.018 | <0.1 |
| +THD 177 (60 mg/L) | 6310 ± 78 | 6223 ± 432 | 2.1 ± 0.4 |

[a]µg (Se equivalent)/g

The results obtained in table 4 show that the incorporation of 2-hydroxy-4-methylseleno-butanoic acid in the culture medium, at 60 mg/L, for 48 h makes it possible to enrich with total selenium by a factor of more than 38 000. These results show moreover that selenomethionine constitutes more than 98% of the total selenium.

The invention claimed is:

1. A non-photosynthetic probiotic bacterium enriched with organic selenium comprising a selenomethionine content greater than 100 µg Se/g in dry weight of said non-photosynthetic probiotic bacterium.

2. The non-photosynthetic probiotic bacterium according to claim 1, wherein it is a lactic bacterium.

3. The non-photosynthetic probiotic bacterium according to claim 2, wherein the lactic bacterium is of the genus *Lactobacillus*.

4. The non-photosynthetic probiotic bacterium according to claim 1, further comprising less than 0.5% in dry weight of inorganic selenium.

5. The non-photosynthetic probiotic bacterium according to claim 4, comprising less than 0.2% in dry weight of inorganic selenium.

6. The non-photosynthetic probiotic bacterium according to claim 5, comprising less than 0.1% in dry weight of inorganic selenium.

7. A probiotic composition comprising a non-photosynthetic probiotic bacterium according to claim 1, living or dead.

8. The non-photosynthetic probiotic bacterium according to claim 1, wherein the selenomethionine content is greater than 500 µg Se/g in dry weight of said non-photosynthetic probiotic bacterium.

* * * * *